United States Patent [19]

Matthiessen et al.

[11] Patent Number: 5,611,908

[45] Date of Patent: Mar. 18, 1997

[54] METHOD OF OPERATING AND AMPEROMETRIC MEASURING CELL

[75] Inventors: Hans Matthiessen, Bad Schwartau; Matthias Studer, Pansdorf, both of Germany

[73] Assignee: Drägerwerk Aktiengesellschaft, Lübeck, Germany

[21] Appl. No.: 576,456

[22] Filed: Dec. 21, 1995

[30] Foreign Application Priority Data

Dec. 22, 1994 [DE] Germany ................... 44 45 948.3

[51] Int. Cl.⁶ ................................................. G01N 27/26
[52] U.S. Cl. ...................... 205/775; 205/782.5; 205/793; 204/415; 204/431; 204/432
[58] Field of Search ..................... 205/775, 782.5, 205/793; 204/415, 431, 432

[56] References Cited

U.S. PATENT DOCUMENTS

| | | | |
|---|---|---|---|
| 4,500,391 | 2/1985 | Schmidt | 204/415 |
| 4,614,577 | 9/1986 | Mund et al. | 204/415 |
| 4,961,834 | 10/1990 | Kühn et al. | 204/412 |
| 5,316,648 | 5/1994 | Kühn et al. | 204/415 |

*Primary Examiner*—Bruce F. Bell
*Attorney, Agent, or Firm*—Walter Ottesen

[57] ABSTRACT

The invention relates to a method for operating an amperometric measuring cell which includes at least a measuring electrode 2 and a counter electrode 3 in an electrolyte chamber 4 filled with an electrolyte. The measuring cell is closed off by a permeable membrane 7 with respect to the measurement sample to be detected. The method of the invention improves the run-in performance of the measuring cell 1. The method includes the step of applying a voltage $U_1$ across the electrodes (2, 3) during a first time span $T_1$ starting at a reference time $T_0$. A reference voltage $U_0$ is assumed at the start of the measurement and the voltage $U_1$ is increased relative to the reference voltage $U_0$.

3 Claims, 4 Drawing Sheets

Fig. 3a
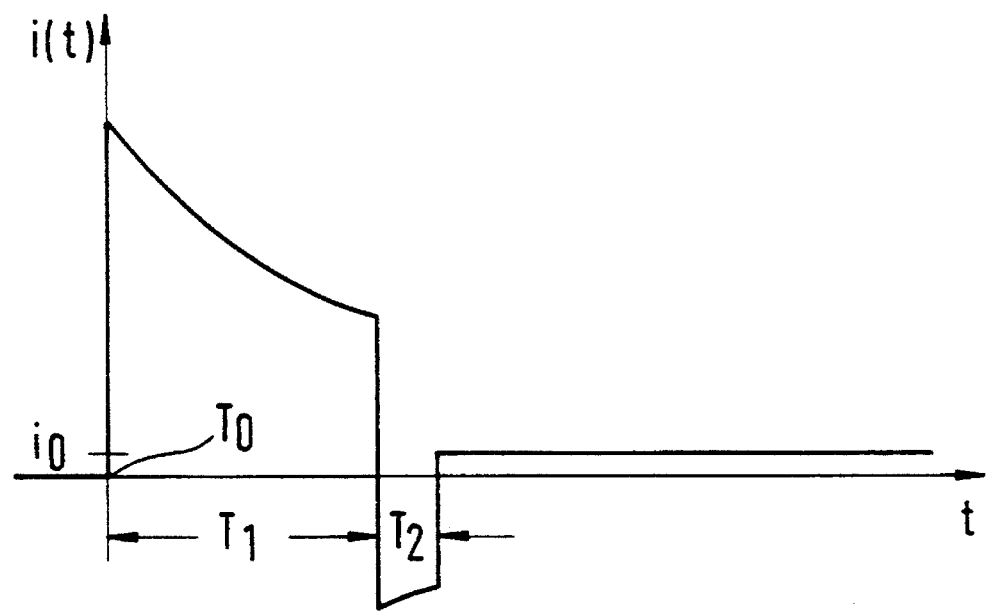
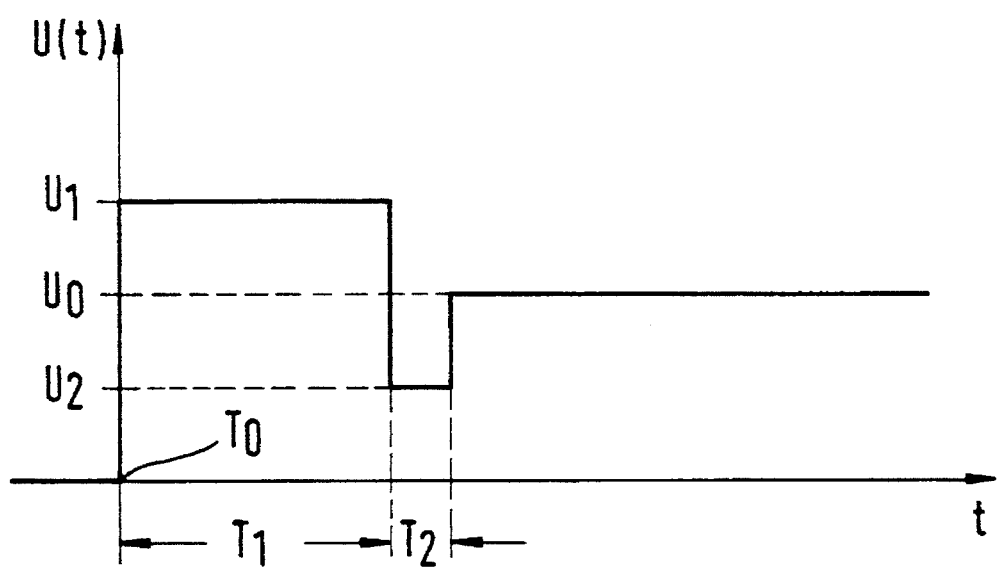
Fig. 3b

METHOD OF OPERATING AN AMPEROMETRIC MEASURING CELL

FIELD OF THE INVENTION

The invention relates to a method for operating an amperometric measuring cell which includes at least a measuring electrode and a counter electrode in an electrolyte chamber which is closed by a permeable membrane with respect to the measurement sample to be detected. The measuring cell is connected to a voltage source supplying a voltage and generating a sensor current between the electrodes.

An electrochemical measuring cell of the above kind is disclosed in U.S. Pat. No. 4,961,834 incorporated herein by reference. In this measuring cell, a measuring electrode, a reference electrode and a counter electrode are arranged in an electrolyte chamber of the measuring cell housing. The electrolyte chamber is filled with an electrolyte and the housing is closed off by a permeable membrane with respect to the measurement sample to be detected. The measuring electrode, the reference electrode and the counter electrode have respective connecting Leads which pass through the measuring cell housing and are connected to an evaluation unit having a voltage source. After the voltage source is switched on, a specific sensor current flows which drops to a steady-state end value after a certain time. This end value can be referred to as the sensor rest current.

It is a disadvantage of this known measuring cell that the sensor rest current is only reached after a longer time and therefore affects the evaluation of the measuring signal by the sensor current which changes continuously and which approaches the sensor rest current asymptotically.

SUMMARY OF THE INVENTION

It is an object of the invention to provide a method for improving the run-in performance of an electrochemical measuring cell.

The method of the invention is for operating an amperometric measuring cell for measuring a sample. The measuring cell includes: an electrolyte chamber having an opening directed toward the sample to be measured and holding an electrolyte; a permeable membrane mounted on the chamber for closing off the chamber; and, a measuring electrode and a counter electrode disposed in the chamber so as to be in spaced relationship to each other. The method includes the steps of: providing a voltage source outputting a voltage U for applying the voltage U across the electrodes to generate a sensor current $i(t)$ between the electrodes; and, starting with the voltage U across the electrodes at a reference voltage $U_0$ at a reference time $T_O$ and applying a voltage $U_1$ during a first time span $T_1$ measured from the reference time $T_O$ with the voltage $U_1$ being increased relative to the reference voltage $U_0$.

The advantage of the invention is seen essentially in that a significantly shortened run-in time is provided for the electrochemical measuring cell by altering the voltage on the electrodes of the measuring cell to a first voltage $U_1$ during a first time span $T_1$. This first voltage $U_1$ is increased compared to the reference voltage $U_0$. The improvement is produced in that the capacitors, which are defined by the electrodes of the measuring cell with the electrolyte disposed therebetween, are charged to the reference voltage $U_1$ more rapidly by the changed voltage so that the sensor current $i(t)$ adjusts more rapidly to the sensor rest current $i_0$. The electrolyte can be in a solid form as a solid-state electrolyte. The electrolyte can also be in liquid form or be a gel.

An advantageous embodiment of the invention comprises applying a second voltage $U_2$ to the electrodes during a second time span $T_2$ which follows the first time span $T_1$ with the second voltage $U_2$ reduced with respect to the reference voltage $U_0$. The time spans $T_1$ and $T_2$ are selected so that the second time span $T_2$ is not greater than the first time span $T_1$. A further shortening of the run-in time of the measuring cell is obtained by dropping the voltage U below the reference voltage $U_0$ during the second time span $T_2$.

The voltages $U_1$ and $U_2$ and the time spans $T_1$ and $T_2$ are so selected that the product of the amount of the difference $U_1$ minus $U_0$ and $T_1$ divided by the product of the amount of the difference $U_2$ minus $U_0$ and $T_2$ is equal to or greater than five as expressed below:

$$\frac{|U_1 - U_0| \cdot T_1}{|U_2 - U_0| \cdot T_2} \geq 5.$$

BRIEF DESCRIPTION OF THE DRAWINGS

The invention will now be described with reference to the drawings wherein:

FIG. 2b shows the graph of voltage $U(t)$ versus time (t) corresponding to the plot of sensor current shown in FIG. 2a;

FIG. 3a shows the sensor current $i(t)$ plotted as a function of time when a voltage $U_1$ is applied which is increased with respect to the reference voltage $U_0$ during time span $T_1$ and reduced to voltage $U_2$ in time span $T_2$ (begin new paragraph) FIG. 3b shows a graph of the voltage $U(t)$ plotted as a function of time (t) corresponding to the plot of sensor current shown in FIG. 3a;

DESCRIPTION OF THE PREFERRED EMBODIMENTS OF THE INVENTION

Figure 1:
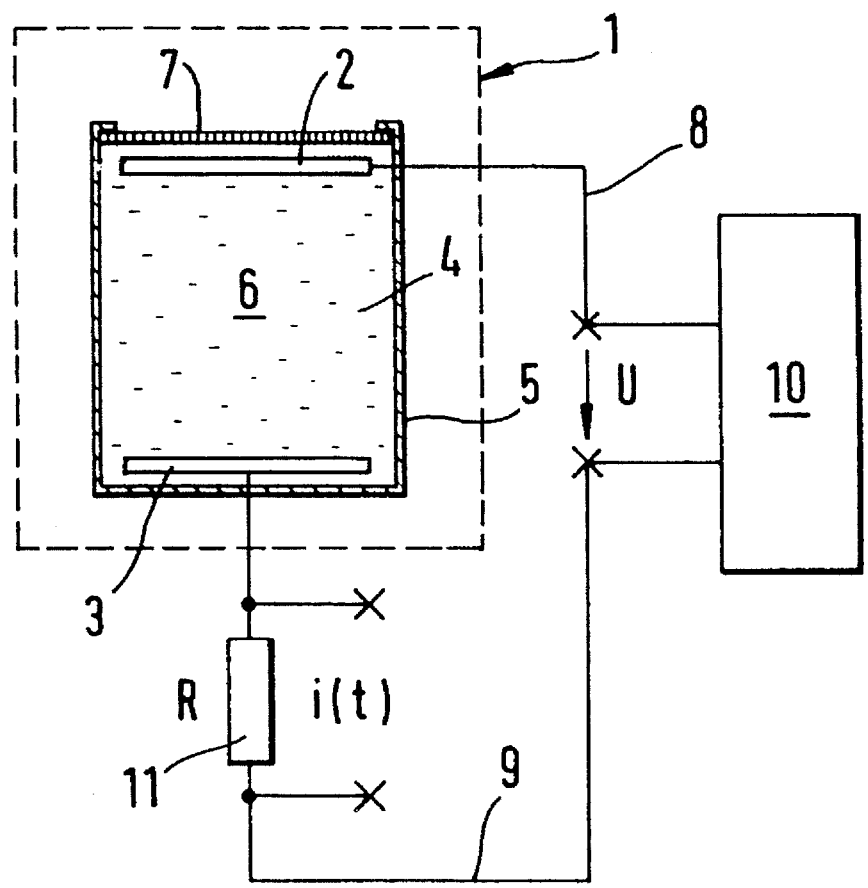
FIG. 1 is a schematic of an amperometric measuring cell having two electrodes.

FIG. 1 shows a schematic configuration of an electrochemical measuring cell 1 having a measuring electrode 2 and a counter electrode 3. The electrodes (2, 3) are arranged in an electrolyte chamber 4 of a housing 5 of the measuring cell 1. The measuring cell housing 5 is filled with an electrolyte 6 in the form of an aqueous solution and is closed off with respect to the gas sample to be detected by a permeable membrane 7. The electrodes (2, 3) are connected via lines (8, 9) to a voltage source 10. A voltage U is applied across the electrodes (2, 3) by means of the voltage source 10. The sensor current $i(t)$ is tapped off as a voltage drop across a measurement resistor 11 in the line 9.

Figure 2A:
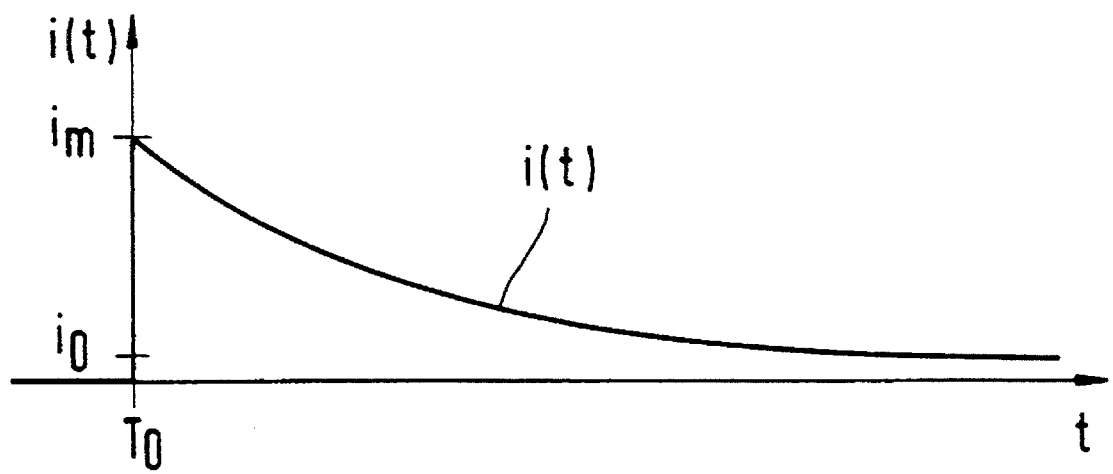
FIG. 2a shows the sensor current $i(t)$ plotted as a function of time when a reference voltage $U_0$ is applied with the latter being constant on a graph of voltage $U(t)$ versus time (t)
Figure 2B:
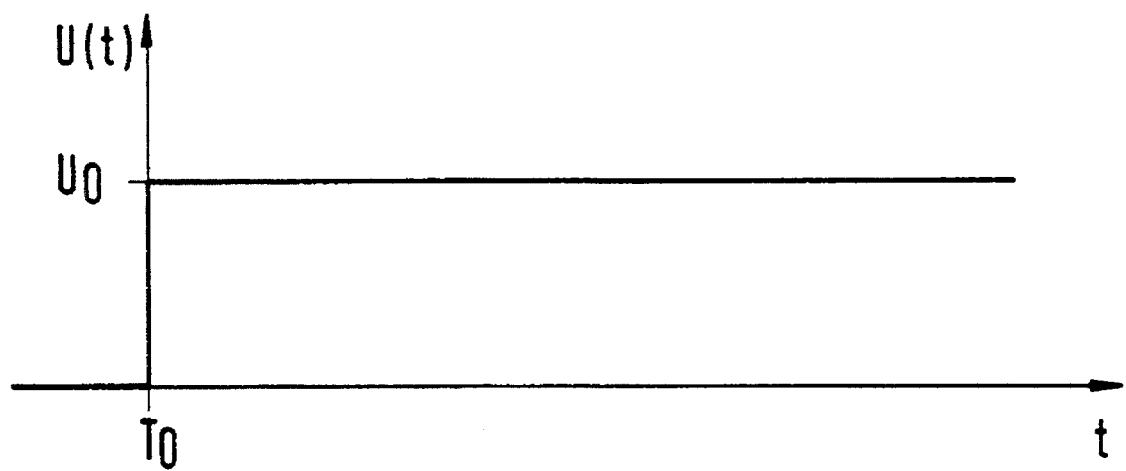

FIGS. 2a and 2b show the sensor current $i(t)$ as a function of time when a constant reference voltage $U_0$ is applied across the electrodes (2, 3) at time point $t=T_0$. The time $T_O$ is coincident with the origin of the coordinates. The sensor current $i(t)$ first increases to a maximum value $i_m$ and then drops to the sensor rest current $i_0$. The time span until the sensor rest current $i_0$ is reached is dependent upon the construction of the measuring cell 1 and can be up to 24 hours. In this way, a continuously changing sensor current i(t) must be accepted during this time interval after the measuring cell 1 is taken into service. This changing sensor current i(t) affects the evaluation of a concentration measurement.

FIGS. 3a and 3b show the run-in performance of the measuring cell 1 operated pursuant to the method of the invention. During a first time span $T_1$, a voltage $U_1$ is applied to the electrodes (2, 3) with this voltage $U_1$ being increased with respect to the reference voltage $U_0$. A second voltage $U_2$ is switched on to the electrodes (2, 3) during a second time span $T_2$ and this voltage $U_2$ is less than the reference voltage $U_0$.

In the present case, the first voltage $U_1$ corresponds to the value of the reference voltage $U_0$ multiplied by a factor of 1.5 and the first time span $T_1$ amounts to approximately 1 hour. The second voltage $U_2$ is adjusted to half the value of the reference voltage $U_0$ and the second time span $T_2$ is approximately 12 minutes.

The sensor current i(t) reaches the sensor rest current $i_0$ already after approximately one hour and 12 minutes as shown in FIG. 3a. This compares favorably to the 24 hours which are needed utilizing the state of the art as shown in FIGS. 2a and 2b.

Figure 4:
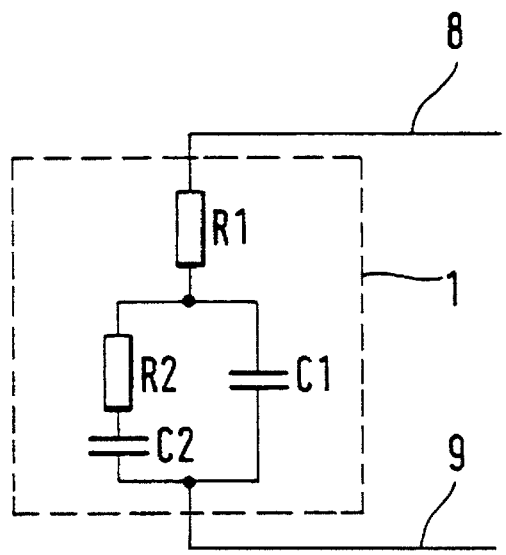
FIG. 4 shows an equivalent circuit of the measuring cell of FIG. 1.

FIG. 4 shows an equivalent circuit of the measuring cell 1 of FIG. 1 and the method of the invention will now be explained with respect to FIG. 4. The elements of the measuring cell 1 are here represented as electrically equivalent resistors and capacitors. $R_1$ is an input and contact resistor of the measuring electrode 2 and $C_1$ is a capacitor defined by the electrodes (2 and 3) and the electrolyte 6. The time constants at which the Faraday current in the measuring cell 1 decays can be represented by a series circuit of a resistor $R_2$ and a capacitor $C_2$ in the equivalent circuit.

The capacitor $C_2$ charges slower than the capacitor $C_1$ when a voltage U is applied across the lines (8, 9). This is so because of the series circuit of the resistors $R_1$ and $R_2$.

Applying the first potential $U_1$ across the lines (8, 9) of the measuring cell 1 causes the charging of the capacitor $C_2$ to be accelerated. It is especially advantageous when the capacitor $C_2$ reaches the reference voltage $U_0$ after the first time span $T_1$ has elapsed. The application of the second voltage $U_2$ during the second time span $T_2$ causes the voltage on the capacitor $C_1$ to again drop to the reference voltage $U_0$. The voltage of the capacitor $C_1$ had a higher value than the reference voltage $U_0$ during the first time span $T_1$. After the time spans $T_1$ and $T_2$ have elapsed, the capacitors $C_1$ and $C_2$ are charged to the reference voltage $U_0$ and the sensor current i(t) assumes its sensor rest current $i_0$ directly after the end of the second time span $T_2$.

The voltages $U_1$ and $U_2$ as well as the time spans $T_1$ and $T_2$ are, in this present case, so selected that the product of the amount of the difference $U_1$ minus $U_2$ and $T_1$ divided by the product of the amount $U_2$ minus $U_0$ and $T_2$ is equal to five as follows:

$$\frac{|U_1 - U_0| \cdot T_1}{|U_2 - U_0| \cdot T_2} \geqq 5.$$

Figure 5:
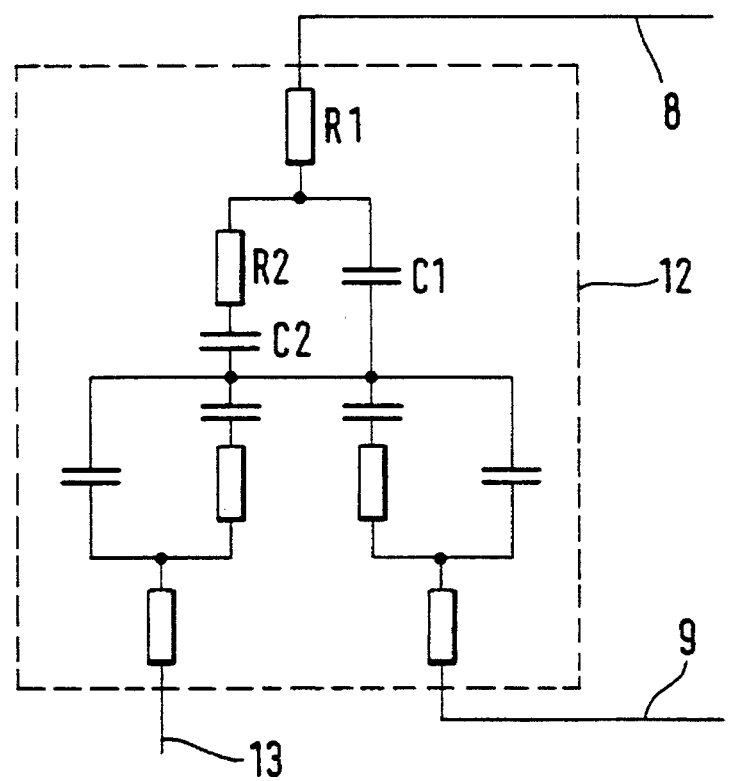
FIG. 5 shows an equivalent circuit of an electrochemical measuring cell having an additional reference electrode.

The method of the invention is applicable in the same manner to a three-electrode measuring cell 12 having a reference electrode. The equivalent circuit of such a measuring cell is shown in FIG. 5. The same components of FIG. 5 are shown with the same reference numerals as in FIGS. 1 and 4. The reference electrode (not shown in FIG. 5) is connected to a line 13 of the three-electrode measuring cell 12.

It is understood that the foregoing description is that of the preferred embodiments of the invention and that various changes and modifications may be made thereto without departing from the spirit and scope of the invention as defined in the appended claims.

What is claimed is:

1. A method of operating an amperometric measuring cell for measuring a sample, the measuring cell including: an electrolyte chamber having an opening directed toward the sample to be measured and holding an electrolyte; a permeable membrane mounted on said chamber for closing off said chamber; and, a measuring electrode and a counter electrode disposed in said chamber so as to be in spaced relationship to each other; and, the method comprising the steps of:

providing a voltage source outputting a voltage U for applying said voltage U across said electrodes to generate a sensor current i(t) between said electrodes; and, starting with said voltage U across said electrodes at a reference voltage $U_0$ at a reference time $T_O$ and applying a voltage $U_1$ during a first time span $T_1$ measured from said reference time $T_O$ with said voltage $U_1$ being increased relative to said reference voltage $U_0$, wherein the sensor current i(t) adjusts more rapidly to a sensor rest current $i_0$ to shorten the run time of the cell.

2. The method of claim 1, further comprising the step of applying a second voltage $U_2$ across said electrodes during a second time span $T_2$ directly after said first time span $T_1$ with said second voltage $U_2$ being dropped relative to said reference voltage $U_0$; and, selecting said first and second time spans ($T_1$, $T_2$) so that said second time span $T_2$ is not greater than said first time span $T_1$.

3. The method of claim 2, wherein said voltages ($U_1$ and $U_2$) and said time spans ($T_1$ and $T_2$) are so selected that the product of the difference ($U_1-U_0$) and $T_1$ divided by the product of the difference ($U_2-U_0$) and $T_2$ is equal to or greater than 5 as follows:

$$\frac{|U_1 - U_0| \cdot T_1}{|U_2 - U_0| \cdot T_2} \geqq 5.$$

* * * * *

UNITED STATES PATENT AND TRADEMARK OFFICE
CERTIFICATE OF CORRECTION

PATENT NO. : 5,611,908

DATED : March 18, 1997

INVENTOR(S) : Hans Matthiessen and Matthias Studer

It is certified that error appears in the above-identified patent and that said Letters Patent is hereby corrected as shown below:

On the title page, in the title, item [54]: delete "AND" and substitute -- AN -- therefor.

In column 1, line 1, in the title: delete "AND" and substitute -- AN -- therefor.

In column 1, line 23: delete "Leads" and substitute -- leads -- therefor.

In column 2, line 5: delete "the," and substitute -- the -- therefor.

In column 2, line 37: delete "(begin new paragraph)" and substitute -- ; -- therefor.

Signed and Sealed this

Twentieth Day of May, 1997

*Attest:*

BRUCE LEHMAN

*Attesting Officer*       *Commissioner of Patents and Trademarks*